US00PP17543P2

(12) United States Plant Patent
Friday

(10) Patent No.: US PP17,543 P2
(45) Date of Patent: Apr. 3, 2007

(54) PEACH TREE NAMED 'P.F. 5D BIG'

(50) Latin Name: *Prunus persica*
Varietal Denomination: P.F. 5D Big

(76) Inventor: Paul Jan Friday, P.O. Box 850, Coloma, MI (US) 49038

( * ) Notice: Subject to any disclaimer, the term of this patent is extended or adjusted under 35 U.S.C. 154(b) by 0 days.

(21) Appl. No.: 10/980,810

(22) Filed: Nov. 4, 2004

(51) Int. Cl.
*A01H 5/00* (2006.01)

(52) U.S. Cl. ..... Plt./197
(58) Field of Classification Search ..... Plt./197
See application file for complete search history.

(56) References Cited

U.S. PATENT DOCUMENTS

PP9,129 P * 5/1995 Friday ..... Plt./197
PP9,850 P * 4/1997 Friday ..... Plt./197
PP10,490 P * 7/1998 Friday ..... Plt./197

OTHER PUBLICATIONS http://www.flaminfury.com/?action=147 Paul Friday's Flamin' Fury Peaches Testimonials.*
http://www.flaminfury.com/?action=149 Paul Friday's Flamin' Fury Peaches Flamin' Fury Varieties.*

* cited by examiner

*Primary Examiner*—Wendy Haas

(57) ABSTRACT

A new and distinct variety of peach *Prunus persica,* tree having the following unique combination of desirable features.

1. The new and distinct variety of peach tree is of moderate upright growth and a regular and productive bearer of semi-cling peaches.
2. Producing a very firm fruit having a resilient flesh texture.
3. A substantially spherical fruit with an attractive red skin coloring over a majority of the surface.
4. Very early maturing fruit of good taste.
5. A very early maturing fruit of good storage and shelf life.

1 Drawing Sheet

Botanical classification: *Prunus persica.*
Variety denomination: 'P.F. 5D Big'.

ORIGIN OF VARIETY

The new peach tree (hereinafter referred to as the 'P.F. 5D Big' peach tree) was originated by Paul Friday in an experimental orchard, which is maintained for the purpose of breeding peach trees, located in Coloma, Mich. Coloma is located in the southwest section of Michigan, USDA Hardiness Zone 6a, with observed temperature ranges of minus 12 degree Fahrenheit to 90 degree Fahrenheit, also annual rainfall of about 40 inches.

In an ongoing mass selection breeding program, unpatented superior seedlings of unrecorded parentage are maintained as seed sources for the production of seeds which are collected and planted in mass. The seed producing parent trees are maintained solely as proprietary trees for breeding purposes and have not been released from the experimental orchard, where such trees can be evaluated for their adaptability to local and regional growing conditions. Seeds resulting from open pollination of the trees in the experimental orchard are regularly planted in mass to produce new populations of seedlings, which are cultured and monitored to maturity. Trees with superior attributes are retained for further observation and testing, and contribute seeds to a advancing generations of new populations of seedlings.

The tree of this application, 'P.F. 5D Big', was a selection from one such unpatented seedling population, and was based on the numerous superior genetic attributes of this tree which are described in the botanical descriptions to follow.

The botanical descriptions to follow are believed to represent a reasonably complete botanical description, of the new peach tree, which is sufficiently detailed to distinguish the tree from the most closely related trees within the same market class.

ASEXUAL REPRODUCTION OF THE VARIETY

The new and distinct variety of peach tree was asexually propagated by budding as performed in an experimental orchard located in Coloma, Mich. The asexual propagation demonstrates that such reproductions of the characteristics of the tree are consistent and are established and transmitted through succeeding propagation.

SUMMARY OF THE VARIETY

The new and distinct variety of peach tree is of moderate upright growth and a regular and productive bearer of peaches. The 'P.F. 5D Big' peach tree bears a semi-cling peach of large diameter of about 2¾". The peach is characterized by a shallow suture. The skin color is an attractive red, which extends in mottled form and stripes into an underlying yellow background. The blossoms are characterized by being contracted or partially spread when in full bloom. At the same time the petals of the blossom are of lesser length than the length of petal of the normal showy blossom as exemplified by the 'Loring' (unpatented) peach blossom.

The flesh of the fruit of the present peach tree is firm and is a dull pale yellow. The flesh surrounding the pit is of minimal color. At maturity the peach is spherical having an average diameter of about 2¾".

The fruit has a firm flesh and may be described as resilient to the extent the flesh is yieldable and restorable to its original state when subjected to impact forces which may cause permanent deformities in peaches of the commercial varieties. The firmness of the fruit facilitates handling and packaging of the peaches damaging the same for shipment. This results in less spoilage and also increases the shelf life.

The fruit matures in the very early part of the peach-growing season of southwestern Michigan. The fruit as mentioned heretofore is of pleasing red color over a substantial portion of its surface and has a very attractive appearance.

BRIEF DESCRIPTION OF THE PHOTOGRAPHS

The accompanying photographic illustrations of the new variety show the following:

The top photograph depicts three (3) well-rounded fruit showing an unpronounced suture and a well-rounded blossom end. One specimen of the fruit is bisected at a ninety-degree angle to the plane of the suture with the stone retained in half showing its freestone characteristic and clear yellow flesh. A tape measure is present indicating the large size of the fruit.

The bottom photograph depicts leaves of medium length and width, having notably very fine serrated margins. A tape measure is present, demonstrating the medium size of the leaves.

DESCRIPTION OF VARIETY

The detailed botanical description of the foliage and fruit of the new variety of peach tree is based upon observations of a 10 yr old specimen grown on Bailey rootstocks, grown at Coloma, Mich., with the color terminology, other than the terminology expressed in common terms, are in accordance with the Pantone Matching System (PMS) as used internationally to identify printed colors.

Botanical classification: *Prunus persica,* cultivar 'P.F. 5D Big'.

Tree:
- *Age.*—Ten (10) years.
- *Height.*—Unpruned 10'.
- *Width.*—Unpruned 13'.
- *Size.*—Medium.
- *Vigor.*—Medium.
- *Density.*—Medium, moderate pruning required.
- *Form.*—Moderately spreading.
- *Production.*—Good, requires thinning (produces about 1 bu. per tree per year).
- *Bearer.*—Consistent bearer.
- *Disease resistance to bacterial leaf and fruit spot.*—Very resistant.
- *Rootstock.*—'Bailey' (unpatented) rootstock.

Trunk:
- *Bark color.*—Gray (pantone # 422).
- *Size.*—Medium.
- *Surface.*—Rough.
- *Diameter.*—4" at 15" above ground, at 10 years of age.
- *Lenticels.*—Pronounced.
- *Lenticels color.*—Very light Gray (patone # 400).
- *Lenticels size.*—3/16" to ¼.

Branches:
- *Size.*—Medium to thin 2¼" diameter at 8" from trunk union.
- *Surface.*—Semi smooth.
- *Lenticels per square inch on branch.*—Eight (8).
- *Lenticels color.*—Light Tan (pantone # 475).
- *Crotch angles.*—60 degrees.
- *Branch color.*—Gray (pantone # 422).

Leaves:
- *Size.*—Average Length 8" — average width 1½".
- *Form.*—Lanceolate — pointed.
- *Thickness.*—Medium.
- *Texture.*—Glabrous.
- *Margin.*—Slightly serrated, not pronounced.
- *Petiole length.*—½".
- *Gland.*—Usually 2–3 on either side of basal of leaf & petiole.
- *Gland color.*—Yellow green (pantone # 118).
- *Gland shape.*—Elongated cup.
- *Leaf color.*—Top of leaf dark green (pantone # 378) bottom of leaf light green (pantone # 377).

Flower buds:
- *Size.*—⅜" long ¼" — wide.
- *Diameter.*—¼".
- *Shape.*—Ovoid.
- *Color.*—Pink (Pantone # 243).

Flowers:
- *Blooming period.*—Apr. 16, 2005 to Apr. 22, 2005.
- *Bloom size.*—¾'" diameter.
- *Blood depth.*—7/16" deep.
- *Size of petal.*—⅜" long — ¼" wide.
- *Number of petals.*—Five (5).
- *Shape of petals.*—Ovate.
- *Petal margin.*—Entire.
- *Petal base shape.*—Ovate.
- *Petal apex shape.*—Rounded.
- *Color of petal.*—Top of petal Pink (pantone # 230) Bottom of petal darker pink (pantone # 210).
- *Number of sepals.*—Five (5).
- *Sepal size.*—3/16" long — ⅛" wide.
- *Sepal shape.*—Ovate.
- *Sepal margin.*—Entire.
- *Sepal base.*—Flat.
- *Sepal apex.*—Ovate.
- *Sepal color.*—Light green (pantone # 367).
- *Number of anthers.*—Twenty four (24).
- *Anther color.*—Carmel brown (pantone #138).
- *Number of stamens.*—Twenty four (24).
- *Stamen length.*—¼".
- *Stamen color.*—Very light yellow (pantone # 100).
- *Pistil length.*—5/16".
- *Pistil color.*—Yellow (pantone # 102).
- *Pollen.*—Present.
- *Flower color.*—Pink (pantone #230).
- *Flower per cluster.*—Two (2).
- *Fragrance.*—None present.

Fruit:
- *Maturity when described.*—Firm ripe.
- *Date of first picking.*—Jul. 21, 2003.
- *Date of last picking.*—Jul. 29, 2003.
- *Size.*—Large — average diameter 2¾".
- *Form.*—Spherical.
- *Suture.*—Not pronounced — stays very firm.
- *Weight.*—Average 7.3 oz.

Skin:

*Thickness.*—Medium as compared to the species.

*Texture.*—Medium as compared to the species.

*Tendency to crack.*—None.

*Down.*—Shorter than is typical in species.

*Color.*—Yellow ground cover (pantone # 129) overspread with 85% red (pantone # 228) — mottling where the colors meet.

Flesh:

*Texture.*—Firm, non-melting, free of fiber.

*Ripens.*—Evenly.

*Flavor.*—Very good.

*Aroma.*—Pleasant.

*Eating quality.*—Very good.

*Brix.*—Average 12%.

*Color.*—Pale yellow (pantone # 127).

*Pit cavity color.*—Light yellow (pantone # 127).

Stone:

*Type.*—Semi — freestone.

*Size.*—Average length — 1½", Average width — 1", Average thickness — ¾".

*Form.*—Ovoid.

*Base.*—Straight.

*Apex.*—Pointed.

*Sides.*—Nearly equal.

*Surface.*—Furrowed.

*Color.*—Tan (pantone # 474).

*Tendency to crack.*—None.

*Kernel.*—½" long, 5/16" wide, 1/16" thick.

*Kernel taste.*—Bland taste.

Use: Dessert.

Shipping quality: Excellent.

Keeping quality: Excellent (up to 3½ weeks).

Disease resistance: The fruit is resistant to Brown rot, and bacterial spot.

The tree and its fruit herein described may vary in slight detail as a result of differences in climatic or soil conditions or cultural practices under which the tree may be grown. It is to be understood that the description of the new variety as set forth herein is that of the tree grown under the ecological conditions prevailing at Coloma, Mich.

What is claimed is:

1. A new and distinct variety of peach tree substantially as herein illustrated and described.

* * * * *

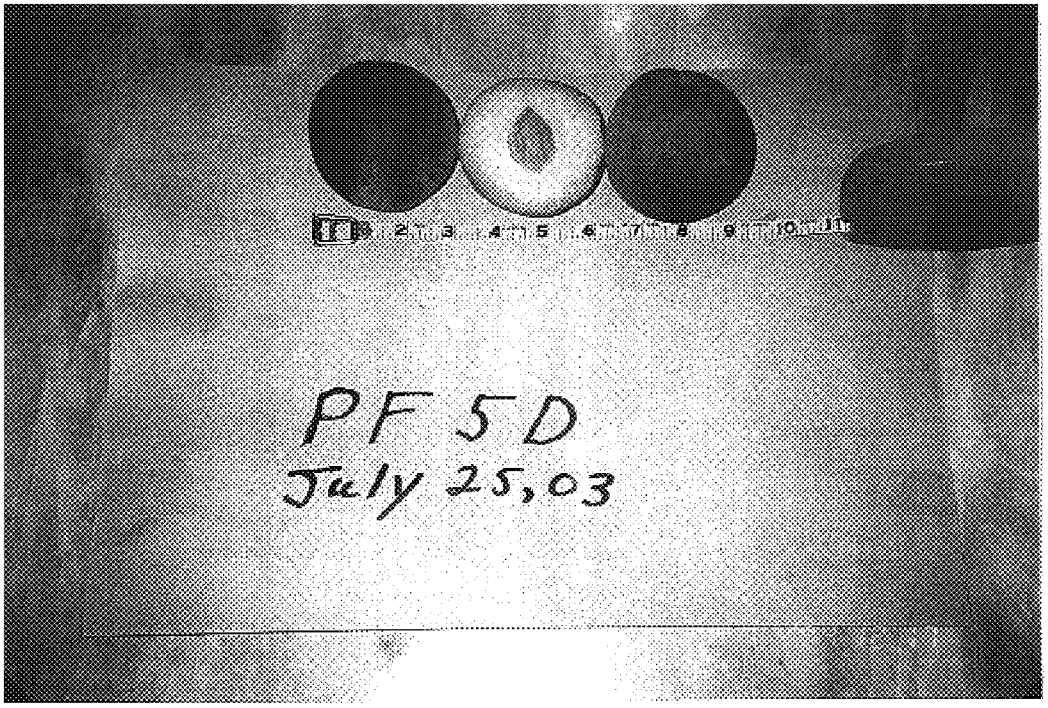
PF 5D
July 25,03
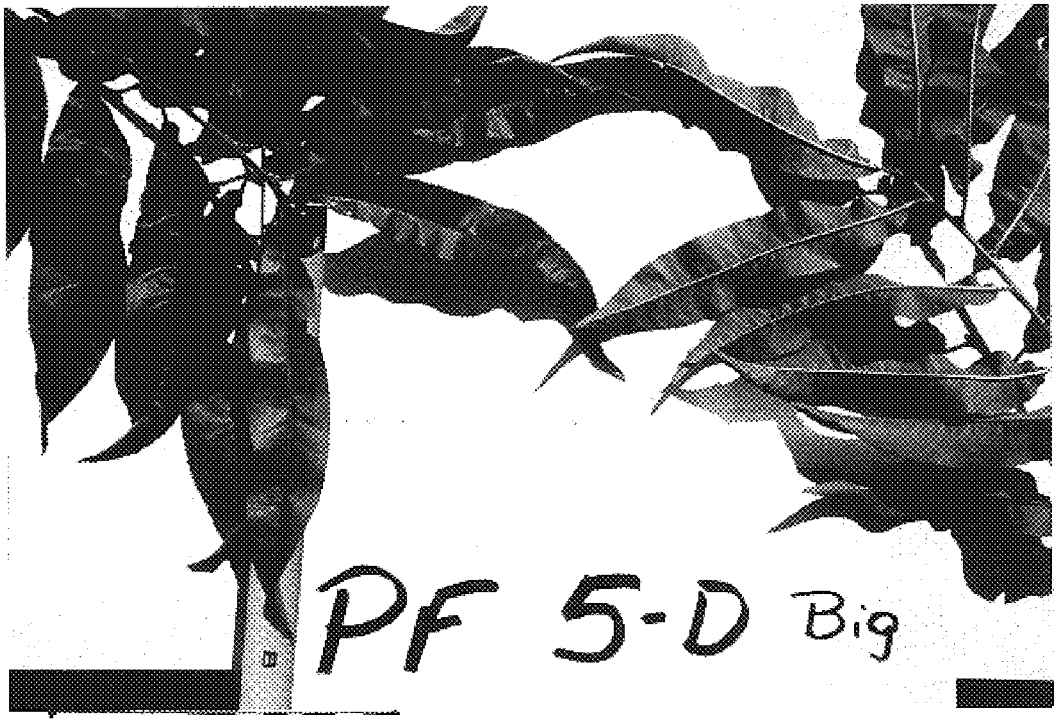
PF 5-D Big